United States Patent [19]

McCoy et al.

[11] 4,264,904
[45] Apr. 28, 1981

[54] FIRE AND ABSENCE DETECTION AND ALARM SYSTEM FOR BED OCCUPANTS

[76] Inventors: Roy G. McCoy, 120 Douglas St., Cartersville, Ga. 30120; James C. Mathis, Hill St., Milan, Tenn. 38358

[21] Appl. No.: 69,593

[22] Filed: Aug. 24, 1979

Related U.S. Application Data

[62] Division of Ser. No. 855,375, Nov. 28, 1977, Pat. No. 4,195,287.

[51] Int. Cl.³ .............................................. G08B 19/00
[52] U.S. Cl. ................................... 340/521; 340/573; 340/584; 340/506; 340/666; 200/85 R
[58] Field of Search ...................... 340/52 E, 506, 521, 340/573, 575, 584, 588, 593, 666; 200/85 R

[56] References Cited

U.S. PATENT DOCUMENTS

| 3,778,805 | 12/1973 | Gould | 200/85 R |
| 4,020,482 | 4/1977 | Feldl | 340/573 |
| 4,075,616 | 2/1978 | Rait | 200/85 R |

Primary Examiner—Alvin H. Waring
Attorney, Agent, or Firm—Nelson E. Kimmelman

[57] ABSTRACT

A bed mat having a sensor for detecting abnormally high temperatures and for detecting when the occupant of the bed is not in it is connected to a control console which has circuits for producing a first electrical signal having a first characteristic in response to the detection of an abnormally high bed temperature and a second signal having a second characteristic in response to the detection of the absence of the bed occupant. In one form of the invention, these signals are applied to the conventional nurse call system to produce sensory signals at the nurses' station, for example, indicative of the detection of high temperature or absence in a way such that they can each be distinguished from the signal produced at the nurse's station by the use of the nurse call button by the patient. Provision is also made for coupling of a smoke detector into the system for actuating the high temperature alarm signaller if smoke is detected.

4 Claims, 7 Drawing Figures

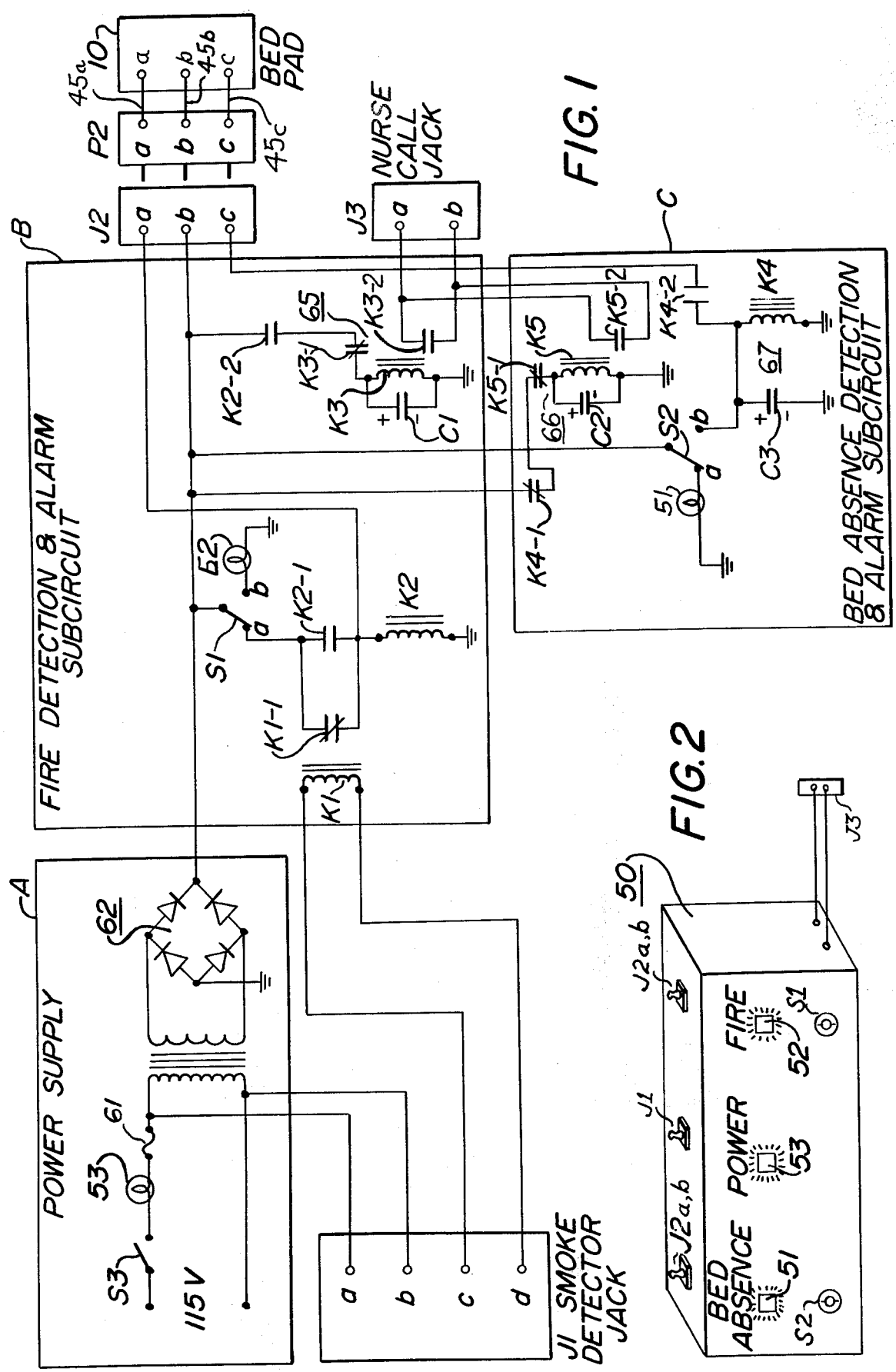

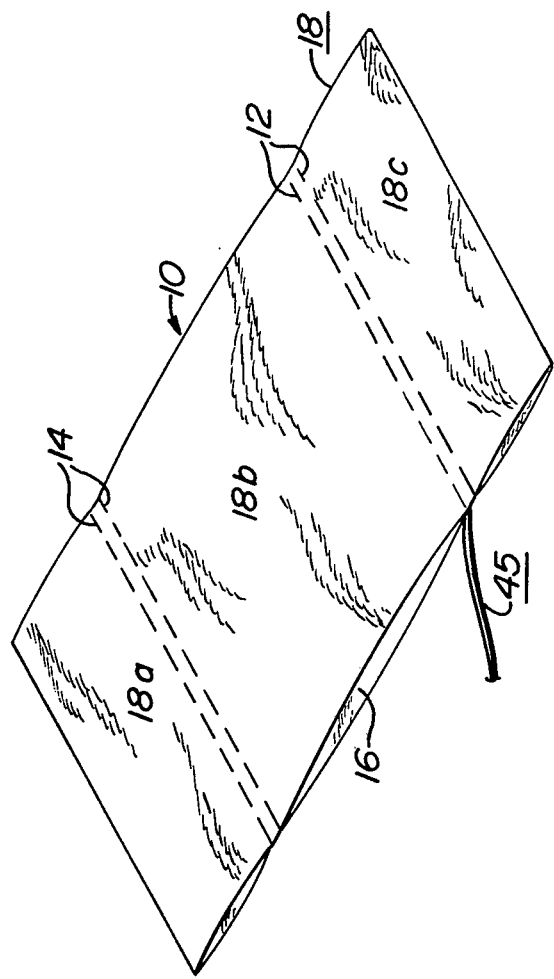
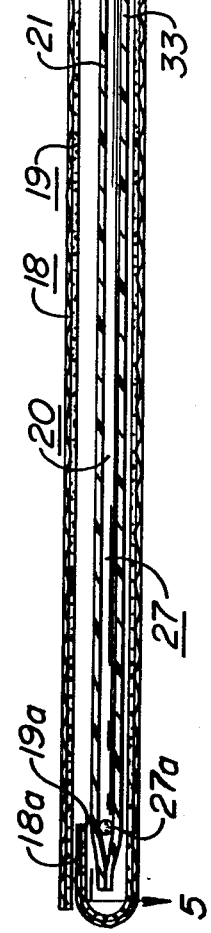
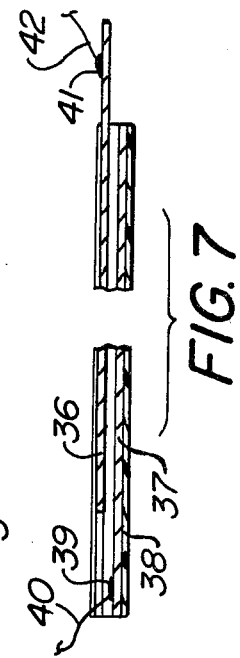
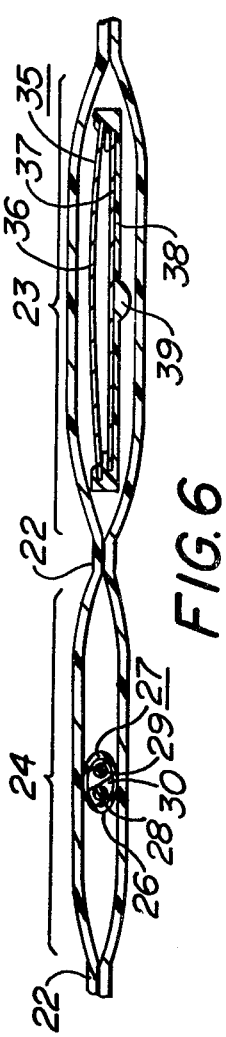

FIRE AND ABSENCE DETECTION AND ALARM SYSTEM FOR BED OCCUPANTS

This is a division of application Ser. No. 855,375 filed Nov. 28, 1977, which matured into U.S. Pat. No. 4,195,287, on Mar. 25, 1980.

BACKGROUND OF THE INVENTION

1. Field of the Invention

This invention relates to systems for safeguarding the persons of bed occupants and in particular to a system for detecting high temperature conditions in a bed and the absence of the occupant thereof and for signalling such unwanted conditions.

2. Prior Art

Systems are known which protect bed occupants by detecting their undesired absence from their beds and producing a signal to alert supervisory personnel. Some of these systems have electrical switches connected to the side rails on the bed which detect when the occupant tries to climb over them. There is some danger to the patient from the electricity present at the switches and from pinching of the patients' fingers. This system is also unable to detect exit from the bed by way of the headboard or footboard.

Other systems (U.S. Pat. No. 3,781,843) have used fluid-filled sensors attached to the tops of the headboard, footboard and side-rails. The pressure in the sensors increases when grasped by the patient as he attempts to get out. With such systems there is always the problem of fluid leaks and the problem of adapting the sensors for securement to the different structural characteristics of different types of beds.

Still other systems use single-function mats of the fluid-pressure-sensing (U.S. Pat. No. 3,727,606) or electrical characteristic types (U.S. Pat. Nos. 2,818,477; 3,760,794; 3,926,177) either to monitor the patient's life signs or detect bed absence. They produce a signal corresponding to the function. No system is known which can, in a single compact sensing mat, detect two different perils and generate two different alarm signals.

It is therefore among the objects of the present invention to provide a dual-purpose bed security system for detection and signalling two different perils to the bed occupant.

Another object is to provide a dual-purpose system which can be associated with any bed of any construction.

Still another object is to provide a dual-purpose system which can be patched into an existing nurse call system and provide two different additional alarm signals distinguishable from the customary signal generated by the patient himself.

Other objects of the invention will occur to those skilled in the art upon perusing the following specification and claims in conjunction with the drawings herein.

SUMMARY OF THE INVENTION

A bed occupant security system comprising sensing means associated with a bed which senses abnormally high temperature conditions therein and which also senses the absence of the occupant thereof. Coupled to the sensing means are first means for producing a first signal in response to said high temperature conditions and second means for producing a second signal responsive to said absence. Provision may optionally be made for coupling into the system a system for detection of combustion products in the neighborhood of the bed.

BRIEF DESCRIPTION OF THE DRAWINGS

FIG. 1 is a schematic diagram of the overall system in accordance with the present invention;

FIG. 2 is a perspective view of a console incorporating most of the components schematically shown in FIG. 1;

FIG. 3 is a perspective view of the novel bed mat according to the present invention;

FIG. 4 is a sectional view taken along the section line 4—4 of FIG. 5 in the direction indicated;

FIG. 6 is a sectional view taken along the section line 6—6 in FIG. 5; and

FIG. 7 is a sectional view taken along the section line 7—7 in FIG. 5.

DETAILED DESCRIPTION OF THE INVENTION—OVERVIEW

Figure 5:
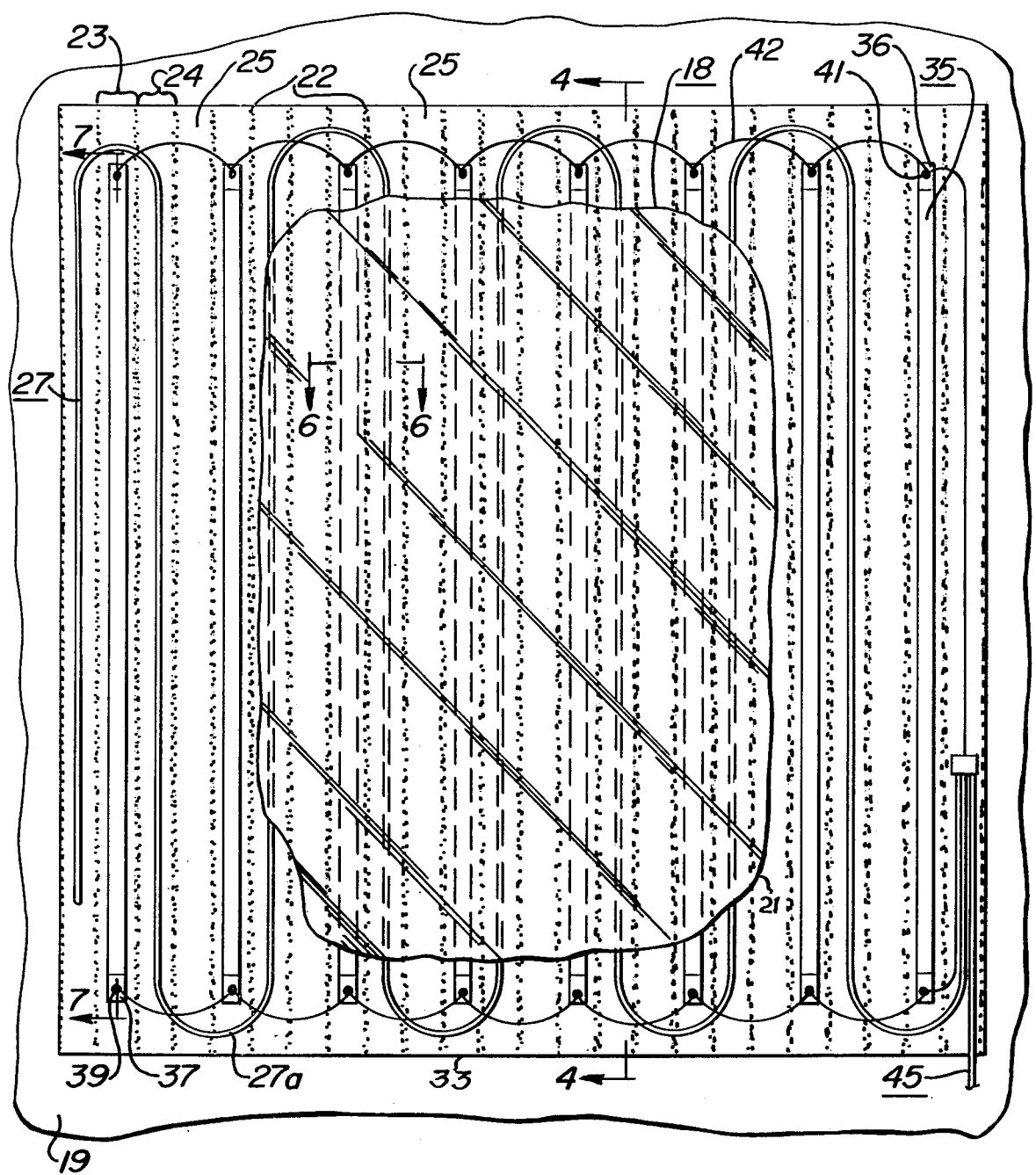
FIG. 5 is a sectional view taken along the line 5—5 in FIG. 4.

As shown in FIG. 1, a novel bed mat 10 is placed under the bed clothing of a patient's bed, for example. This bed mat includes a sensor for detecting abnormally high temperature conditions and another sensor for detecting when the occupant of the bed is not in it. It is connected via plug P2 and jack J2 to a control console 50 (shown in FIG. 2) which incorporates the circuits shown in FIG. 1. The circuits include a power supply A for a fire detection and signalling circuit B and a bed absence detection and signalling circuit C. Circuits B and C are respectively coupled to the fire and bed absence sensors in the bed mat 10. The power supply A also energizes a smoke detector (not shown) through a smoke detector jack J1 and the output of the smoke detector is, itself, applied back to the circuit within console 50 to actuate the same alarm circuit as the one actuated by the fire detection sensor. Both the fire detection and alarm circuit B and the bad absence detection and alarm circuit C have their output electrical signals applied to the nurse call jack J3 which is connected to the nurse call system (not shown). The electrical signals applied to the nurse call light (or other sensory signal) at the nurse's station cause that light to flash at a fast rate in the event of fire and at a slower rate in the event of the absence of the bed occupant. The conventional nurse call is also useable by the patient upon pressing the patient's conventional switch whereupon a constant light signal is produced.

BED MAT CONSTRUCTION

FIGS. 3-7 show the construction of the novel bed pad 10 used in our alarm system which is placed under the sheets of each bed in a nursing home, for example. It has a cover 18 which is folded around an internal sensing mat 20 inserted in its central compartment 18b that is bounded by stitches 12 and 14. Mat 20 has a plastic top sheet 21 and a plastic bottom sheet 33 joined together on all sides. The end 18a of the cover is folded up and inwardly over the left edge of the internal mat 20. Cover 18 has a foot portion 18c extending from the stitching 12 down to the right end and a head portion 18d extending upwards from the stitching 14.

The cover 18 is made of a moisture and flame-resistant material, preferably having some cushioning effect and having a high coefficient of friction so as to prevent sliding under the bed clothes. One material for the cover which meets these requirements is "Allenfoam" produced by Allen Industries, Inc. of Richmond, Va. It has a woven top layer laminated to a foamed elastomer bottom layer. However, other suitable materials may alternatively be used.

The sensing mat 20 is divided by heat-formed seams 22, as shown in FIG. 5, into a number of parallel compartments 23, 24 and 25. The contents of the compartments 23, 24 and 25 are generally the same as they recur cyclically from left to right (FIG. 5). Within the compartments 23 a number of elongated assemblies 35 are disposed for detecting the presence or absence of the occupant of the particular bed involved. The assemblies 35 each comprise an elongated strip of metal 36 having a slightly convex cross-section as shown in FIG. 6 whose longitudinal edges are fixed within a plastic holder 38. The holder 38 also includes a lower metallic strip 37 spaced from the upper strip 36 as shown. As seen in FIG. 7, all of the lower strips 37 are electrically joined together by the wire 40 which is attached to contacts 39 on each strip 37. Similarly, at the other ends, a wire 42 is soldered or otherwise connected to all of the contacts 41 on the upper metallic member 36. Thus, all of the subassemblies 35 are electrically in parallel. When the patient is in the bed, at least one of the assemblies 35 will have its strip 36 touch strip 37 under the weight of the occupant thereby closing a circuit attached to the bed absence alarm. If the patient leaves the bed, there will not be any assembly 35 in mat 20 in which the strips 36 and 37 touch so that this open circuit condition operates to actuate the bed absence alarm as will be explained in detail below. The wires 40 and 42 are connected to the output wires in sheath 45. A mat which has sensing devices such as assemblies 35 may be obtained from the Tapeswitch Company in Connecticut.

In accordance with one feature of our invention, the bed mat also incorporates a fire-sensing device. As shown in FIG. 5, a fire or high temperature sensing element 27 is sinuously disposed between the top 21 and bottom 33 of mat 20. In one form, the detection element may consist of two conductors 28 and 29 placed very close together (as shown in FIG. 6) in a core of plastic 30 within a plastic cover 26. The curved end portions of sensor 27 penetrate the fused seams 22 toward the top and bottom of mat 20 and most of its straight portions are disposed within compartments 24 (except for the left-most portion in FIG. 3 where it is in a compartment 25). The sensor 27 may be, for example, an item known as "Detectifire" made by Company in Massachusetts. However, it should be understood that other types of heat-sensitive sensors may alternatively be disposed within the mat 20. The wire leads 45a, 45b (FIG. 1) for the sensor 27 are also enclosed in the output wire sheath 45 shown in FIG. 3. The conductors 28 and 29 are placed so close to one another in core 30 that high temperature conditions such as caused by a fire (or even a cigarette burn) will cause them to touch and this shorting is effectively a switching action causing actuation of the fire alarm as will be explained below.

The output wires 45a and 45b are connected to two pins of a plug P2 (FIG. 1). Plug P2 is intended to mate with jack J2 whose terminals are separated into two parts on the top of the control console 50 shown in FIG. 2. The terminal b of jack J2 is common to both of the parts of the jack atop console 50.

FIRE DETECTION AND ALARM SIGNAL GENERATION (FIGS. 1 AND 2)

The power supply A is housed within the console 50 and includes a connection to a 115 volt source via a switch S3 in one side of the line which is in series with a fuse 61 and a (white) light 53 which is turned on when the switch S3 is closed. Closure of the switch energizes the primary of transformer T1 which is coupled via a secondary winding to diode bridge 62 that produces at one of its output terminals +24 volts DC. This DC voltage is applied via the mating jack J2-Plug P2 combination and via lead 45b to the terminal b of the bed pad 10. Terminal b is attached, for example, to conductor 28 in the sensing mat 20. Conductor 29 is attached to terminal a of the bed pad 10 which is, in turn, connected to wire 45a that is connected to terminal a of plug P2. When the conductors 28 and 29 are shorted by the melting of the plastic between them, +24 volts DC are applied to terminal a of J2 and thence to ground through relay winding K2 energizing the latter. So energized, winding K2 causes its associated contact K2-1 to change condition, i.e., to close whereupon, if the toggle (or other appropriate) switch S1 has been thrown to its "a" or "on" position, the +24 volt current from the power supply is applied through K2-1 and through K2 so as to latch the latter. When K2 is energized, it will also cause its other associated set of contacts K2-2 to change condition, i.e., to close, whereupon +24 VDC from the bridge 62 is applied through those contacts to the fast flasher circuit. The fast flasher circuit comprises a normally closed set of contacts K3 in series with a parallel capacitative-inductive circuit consisting of capacitor C1 and relay primary winding K3 having common terminals connected to ground. Application of the DC voltage to the positive plate of capacitor $C_1$ will soon charge it up to the full +24 volts (or to some voltage level below that depending upon the requirements of the relay K3). At this point, the relay coil K3 will be energized thereby changing contacts K3-1 to the open position and contacts K3-2 to the closed condition. This shorts the outputs a and b of the nurse call jack J3 thereby causing the light or other signal associated with the nurse call system to go on. When the contacts K3-1 open, capacitor $C_1$ discharges through K3 thereby helping to keep it on for a short time longer depending upon the RC constant of C1-K3. When K3 is deenergized, the condition of contacts K3-1 and K3-2 will again change resulting in the reapplication of +24 volts from the power supply to the C1-K3 combination and the opening of the nurse call contacts by virtue of the opening of contacts K3-2. Thus, there will be an open circuit between terminals a and b of the nurse call jack again so that the nurse call is momentarily inactivated. This process continues at a rapid rate depending upon the value of C1 and K3.

BED ABSENCE ALARM OPERATION

When the patient is in bed, +24 volts from the power supply 62 is applied via the terminal b of J2 and terminal b of P2 to element 36 in the bed mat. The weight of the patient on strip 36 brings it into conductive contact with strip 37 which is connected to terminal c of the bed pad and thence, via terminal c of P2 and J2, to the set of contacts K4-2 which are normally open. With the patient in bed, the arm of switch S2 is turned to the b position whereupon +24 volts from the power supply 62 is applied to the ungrounded end of the relay coil K4 and the positive plate of capacitor C3. Current through K4 causes the normally open contacts K4-2 to close thereby latching K4 "on." At the same time, contacts K4-1 become open so that energization of the slow flasher circuit 66 is cut off.

If, while the switch arm is at b, the patient goes out of the bed during the day time, for example, the position of the switch arm of S2 at contact b will keep the relay coil K4 energized notwithstanding the fact that no current is being applied via closed contacts K4-2. Nor will any voltage appear at terminal c of jack J2. Thus, since relay coil K4 is energized, contacts K4-1 will be open and prevent the slow flasher circuit 66 from being energized.

At night time, when the patient goes back into his bed, the switch arm of S2 is put to the a or "on" position which means that the coil K4 is then energized by the closure of the circuit from the power supply 62 through pressure on the strips 36 and 37 causing them to come into contact. The light 51 will go on and the continuous current through K4-2 will be the only current source to energize the coil K4. If the patient then gets out of bed, the strips 36, 37 do not make electrical contact and hence there will be no current through K4 so that contacts K4-2 will revert to their normally open position whereas contacts K4-1 will revert to their normally closed condition thereby energizing the slow flasher circuit 66.

The energization of the slow flasher circuit is, however, delayed somewhat by the bed alarm delay subcircuit 67 to prevent false alarms due to possibly very brief opening of all of the strips 36, 37 simultaneously. Since the positive plate of C3 has been charged to the power supply voltage when the arm of S2 was in the b position, as soon as the strips 36, 37 separate, the contacts K4-2 do not immediately reopen because the capacitor C3 will discharge through K4 to ground keeping K4 energized for a slight period longer depending upon the value of capacitance of C3 and the resistance value of K4.

After the end of the delay interval and the de-energization of K4, the reclosing of contacts K4-1 causes current to flow through the normally closed contacts K5-1 to the slow flasher subcircuit 66. Current through relay coil K5 changes the condition of contacts K5-1 to open and contacts K5-2 to close thereby closing the circuit across the terminals a, b of nurse call jack J3. This will produce a sensory signal at the nurse's station. The opening of contacts K5-1 causes capacitor C2 to discharge through coil K5 to ground, the discharge time being a function of the capacitance value of C2 and the resistance value of K5. When relay coil K5 becomes de-energized (assuming K4-1 remains closed), contacts K5-1 return to their closed state whereas contacts K5 return to their open state so that the signal at the nurse's call station ceases.

The de-energization of K5 enables the cycle to continue since the power supply voltage will be applied again via K4-1 and the normally closed contacts K5-1 to the slow flasher subcircuit 66 for re-energization of coil K5 and re-charging of capacitor C2 as explained above.

SMOKE DETECTOR OPERATION-NO SMOKE CONDITION

Under recent regulations, it is also necessary to include a smoke detector in invalid or patient care institutions. The input to the smoke detector (not shown) is coupled via terminals a and b of the jack J1 to 115 volts AC from the primary of the power supply transformer T1. In the absence of ambient smoke, the smoke detector will normally produce a 30 milliamp current at the terminals c and d of the smoke detector jack. This energizes relay coil K1 which causes its associated contacts K1-1 to open. Assuming that fire alarm switch S1 is in the a position, since K2-1 are also open, K2 stays deenergized. With K2-1 not energized, contact K2-2 is open so that no current can flow into the fast flasher circuit 65. Of course, if switch S1 is in the b or "off" position, there will also be no current through K2. Thus the operation will be the same as when the smoke detector detects no smoke so that there will be no fast flash signal produced by the output of the fast flasher circuit 65.

SMOKE DETECTION AND FAIL-SAFE CONDITION

If S1 is at the a position (meaning that the bed pad fire alarm is "on") and if smoke is detected by the detector, there will no longer be an output at terminals c and d of the smoke detector jack J1. Therefore, K1 will not be energized so that K1-1 will revert to its normally closed condition. Therefore, +24 volts will be applied via contacts K1-1 through the coil K2 causing associated contacts K2-1 to close thereby latching the relay operation and closing contacts K2-2 which enables energization of the fast flasher circuit 65 in the same manner as explained above in connection with the fire detection and alarm circuit B.

Fail-safe operation is also built in because, if the power supply is not energized, there will be no input to the smoke detector jack J1 at terminals a and b thereof and, accordingly, no output will appear at terminals c and d of that jack. This means that K1 is no longer energized and so contacts K1-1 close whereupon the operation is the same as if smoke had been detected resulting in fast flasher signal output at the nurse call jack terminals a and b.

We claim:
1. A sensing assembly for use in a bed comprising:
   (a) first means comprising a continuous length of two-parallel wires in close proximity to one another but separated by an insulating material which melts at a predetermined temperature higher than normal room temperatures, said first means sensing an abnormally high temperature condition in said bed and being adapted to cooperate with external circuitry to produce a first electrical signal in response thereto, and
   (b) a second means comprising a plurality of discrete pairs of resilient ribbon-like conductors, the conductors of each pair being disposed in spaced vertical relation with one another, said second means sensing the absence of the occupant of said bed and being adapted to cooperate with external circuitry to produce a second electrical signal in response thereto,
   said first and second means being interspersed with one another in substantially a common plane.

2. The sensing assembly according to claim 1 wherein said first means is elongated and sinuously interspersed with said second means, and wherein all of said discrete pairs of resilient conductors are connected in parallel with one another.

3. The sensing assembly according to claim 2 wherein said first means is arranged in an undulating pattern and each undulation winds around one discrete pair of said second means.

4. The sensing assembly according to claim 3 wherein each of said discrete pairs is encased in a separate elongated insulating pocket and wherein said undulating first means has portions disposed in separate elongated insulating pockets generally parallel to said pockets in which said discrete pairs are disposed.

* * * * *